United States Patent [19]

Krenceski et al.

[11] Patent Number: 5,744,703
[45] Date of Patent: Apr. 28, 1998

[54] PROCESS TO MEASURE THE STRINGINESS OF ROOM TEMPERATURE VULCANIZABLE SILICONE SEALANT COMPOSITIONS

[75] Inventors: Mary A. Krenceski, Troy; Chiu-Sing Lin, Schenectady; Gary M. Lucas, Scotia, all of N.Y.

[73] Assignee: General Electric Company, Waterford, N.Y.

[21] Appl. No.: 805,517

[22] Filed: Feb. 26, 1997

[51] Int. Cl.[6] ................................................. G01N 11/02
[52] U.S. Cl. ............................ 73/54.01; 73/87; 73/866
[58] Field of Search ........................... 73/54.01, 64.41, 73/64.43, 64.56, 783, 866, 169, 150 A, 150 R, 827, 834

[56] References Cited

U.S. PATENT DOCUMENTS

| | | | |
|---|---|---|---|
| H976 | 11/1991 | Matta et al. | 73/866 |
| 2,904,994 | 9/1959 | Claxton | 73/150 |
| 3,747,397 | 7/1973 | Sharabash | 73/150 R |
| 3,759,089 | 9/1973 | Sharabash | 73/150 R |
| 3,789,660 | 2/1974 | Rubio et al. | 73/169 |
| 4,247,442 | 1/1981 | Shimizu . | |
| 4,304,897 | 12/1981 | Bluestein . | |
| 5,162,407 | 11/1992 | Turner . | |
| 5,371,162 | 12/1994 | Konings et al. . | |
| 5,583,178 | 12/1996 | Oxman et al. . | |

*Primary Examiner*—Ronald L. Biegel
*Attorney, Agent, or Firm*—Kenneth S. Wheelock

[57] ABSTRACT

A standardized test for measuring the stringiness of room temperature vulcanizable silicone sealant compositions is disclosed wherein a tube of sealant is held at a constant angle to the surface upon which the sealant is being applied. The surface is movable and once a small bead of sealant has been deposited upon the surface the surface is moved at a constant rate of speed until the sealant bead breaks off from the source. The length of any string of sealant formed thereby is measured. This measurement for a given composition is compared to the measurement for other compositions and thereby allows optimization of sealant compositions to minimize an undesirable feature.

2 Claims, No Drawings ns. More particularly the present invention relates to the

PROCESS TO MEASURE THE STRINGINESS OF ROOM TEMPERATURE VULCANIZABLE SILICONE SEALANT COMPOSITIONS

FIELD OF THE INVENTION

The present invention relates to room temperature vulcanizable silicone sealant compositions that exhibit stringiness. More particularly the present invention relates to the process of measuring the stringiness of such compositions that cure by condensation of acyloxy or alkoxy terminated polydiorganosiloxane polymers.

BACKGROUND OF THE INVENTION

Organopolysiloxane room temperature vulcanizable (RTV) compositions that are stored under anhydrous conditions will cure upon exposure to water or water vapor at room temperature to yield elastomers. These RTV compositions are prepared by mixing diorganopolysiloxanes having reactive end groups with organosilicon compounds that possess at least three hydrolyzable reactive moieties per molecule. The known RTV compositions are widely used as elastic sealing materials for applications involving the gaps between various joints such as the gaps between the joints of building materials, the joints between structural bodies and building materials in buildings, between the bathtub and wall or floor, cracks on tiles in bathrooms, gaps in the bathroom such as those around the washbasin and those between the washbasin supporting board and the wall, gaps around the kitchen sink and the vicinity, between panels in automobiles, railroad vehicles, airplanes, ships, gaps between prefabricated panels in various electric appliances, machines, and the like. Room temperature vulcanizable silicone sealants thus may be utilized in a wide variety of caulking and sealing applications.

As a caulking material these sealants are frequently filled with finely divided inorganic materials which may be either reinforcing or non-reinforcing. Reinforcing fillers may be fumed silica, precipitated silica, hydrophobicized precipitated silica, hydrophobicized fumed silica, carbon black, titanium dioxide, ferric oxide, aluminum oxide, and other metal oxides. Non-reinforcing fillers may be calcium carbonate, diatomaceous earth, calcium silicate, zirconium silicate, talc, and bentonite. Fibrous materials such as asbestos, glass fibers, or organic fibers are also useful fillers. The amount of filler used in an RTV composition is selected as desired so as to not interfere with the purposes of the instant invention.

When it is anticipated that these sealant materials will be exposed to conditions that will tend to degrade performance or appearance over a period of time, these sealants are frequently stabilized against such a deterioration by the addition of small quantities of protective additives such as UV stabilizers, anti-oxidants, fungicides, and the like. These additives tend to complement the physical property profile of the sealant by adding additional desirable properties, e.g., resistance to photocatalytic degradation, oxidation (flame retardants), and attack by fungi.

Various compounds have been added to the formulations of RTV sealants to improve performance with respect to one or another property. For example, U.S. Pat. No. 4,247,442 discloses and claims the incorporation of various benzimidazoles to reduce the growth of fungus and mildew on the surface of the sealants. Because the benzimidazole compounds are insoluble in water, the incorporation of benzimidazole compounds by themselves was not satisfactory. Incorporation of a small amount of an organic surfactant rendered the benzimidazole compounds wettable thereby enabling the functioning of the compounds as mildewcides and fungicides.

U.S. Pat. No. 4,304,897 discloses room temperature vulcanizable silicone sealants containing a silicone polyether copolymer. Such silicone polyether copolymers are added to the one component RTV compositions in order to reduce the flow properties of the uncured sealant when it is applied to a surface. When such a silicone polyether copolymer was used in the RTV composition, the flow of the silicone sealant after application was significantly decreased, as measured in a Boeing Flow Jig.

U.S. Pat. No. 5,162,407 discloses the use of fluorocarbon surfactants to reduce the tendency of the components of an RTV rubber to migrate and separate during the evaporative stage of curing. The utility of adding a fluorocarbon surfactant is particularly pronounced when the RTV is applied to a smooth, non-porous substrate such as glass. Thus, surfactants have been added to RTV compositions for a multiplicity of purposes and objectives.

A continuing problem with RTV sealant compositions is the tendency of the composition to form threads of silicone sealant during application even after application has stopped. This phenomenon has been named stringiness. While the silicone sealant extrudes from a caulking tube or other application device in a fairly uniform fashion while a delivery pressure is being applied, a cessation of the delivery force does not yield a clean cut off of the silicone bead formed by the application apparatus. The sealant has a tendency to string out from the nozzle of the delivery mechanism. This causes problems in appearance requiring extensive tooling to render the sealant bead both functional and attractive. More importantly, the string or thread that results after a delivery pressure has been stopped wastes silicone sealant. This problem, referred to hereafter as a stringiness problem is a continuing problem.

SUMMARY OF THE INVENTION

The present invention provides for a process for measuring the stringiness of uncured room temperature vulcanizable sealant compositions comprising:

(a) delivering said sealant onto a movable surface by means of a sealant delivery device whereby a bead of sealant is deposited onto said movable surface;

(b) stopping the delivery of said sealant onto said movable surface;

(c) moving said bead of sealant on said movable surface away from said sealant delivery device by moving said movable surface away from said sealant delivery device whereby a string of sealant is formed between said bead of sealant and said sealant delivery device until said siring of sealant breaks off from said sealant delivery device;

(d) stopping said movable surface; and (e) measuring the length of said string of sealant.

The present invention further provides for a method of selecting a sealant composition for a particular sealant application from a plurality of sealant compositions comprising:

(a) setting a minimum performance level for said application;

(b) calibrating said minimum performance level for said application to a maximum or minimum length of a siring of sealant as measured by the process measuring stringiness for each sealant; and (c) determining which sealants of said group of sealant compositions satisfy said minimum performance level for said application.

The process of the present invention is particularly useful when it is used to measure the stringiness of sealants having a composition comprising:

(A) an organopolysiloxane having the formula:

HO(RR'SiO)$_x$H wherein R and R' are independently selected monovalent hydrocarbon radicals having from one to forty carbon atoms, where x has a value whereby the viscosity of the organopolysiloxane is about 500 to 200,000 centipoise at 25° C.:

(B) an organosilicon compound having at least two hydrolyzable moieties per molecule or their partial hydrolysis products selected from the group of compounds having the formulas:

R$_a$Si(ON=CR'$_2$)$_{4-a}$, where R and R' are independently selected one to forty carbon atom monovalent hydrocarbon radicals, and a is 0, 1 or 2;

R$_a$Si(OR')$_{4-a}$, where R and R' are independently selected one to forty carbon atom monovalent hydrocarbon radicals, and a is 0, 1 or 2;

R$_a$Si(OCOR')$_{4-a}$, where R and R' are independently selected one to forty carbon atom monovalent hydrocarbon radicals, and a is 0, 1 or 2;

R$_a$Si(NR'R")$_{4-a}$, where R and R' are independently selected one to forty carbon atom monovalent hydrocarbon radicals, R" is hydrogen or the same as R, and a is 0, 1 or 2; and R$_a$Si(NR'"COR')$_{4-a}$, where R and R' are independently selected one to forty carbon atom monovalent hydrocarbon radicals, R'" is an independently selected one to forty carbon atom monovalent hydrocarbon radical, and a is 0, 1 or 2;

(C) a non-ionic surfactant compound selected from the group of non-ionic surfactants consisting of polyethylene glycol, polypropylene glycol, ethoxylated castor oil, oleic acid ethoxylate, alkylphenol ethoxytates, copolymers of ethylene oxide (EO) and propylene oxide (PO) and silicone polyether copolymers;

(D) a reinforcing filler; and (E) a condensation cure catalyst.

DETAILED DESCRIPTION OF THE INVENTION

The present invention is associated with the discovery that acetoxy, ketoximo, and alkoxy silicone sealants incorporating a particular class of surfactant compounds unexpectedly show reduced stringiness. The level of incorporation of the surfactant compounds ranges from about 0.10 percent by weight to about 3.00 percent by weight, more preferably from about 0.50 percent by weight to about 1.50 percent by weight, and most preferably from about 0.60 percent by weight to about 1.00 percent by weight of the total composition.

In general, one component RTV silicone sealants of the present invention comprise:

(A) an organopolysiloxane having the general formula

HO(RR'SiO)$_x$H wherein R and R' are substituted or unsubstituted monovalent hydrocarbon radicals having from one to forty carbon atoms which may be identical or different, i.e. R and R' are independently selected, where x has a value such that the viscosity of the organopolysiloxane is about 500 to 200,000 centipoise at 25° C. A portion of the hydroxyl groups may be replaced by other reactive end groups or endstoppers such as organoketoxime groups, carboxyl groups, acetoxy groups, RNH-groups, (where R is as previously described), carbamoyl groups, alkoxy groups, alkylalkoxy groups, or arylalkoxygroups;

(B) an organosilicon compound having at least two hydrolyzable moieties per molecule or their partial hydrolysis products having variously the following formulae prior to partial hydrolysis:

R$_a$Si(ON=CR'$_2$)$_{4-a}$,

R$_a$Si(OR')$_{4-a}$,

R$_a$Si(OCOR')$_{4-a}$ where R and R' are the same as defined previously and may be independently selected for each compound, and a is 0, 1 or 2, R$_a$Si(NR'R")$_{4-a}$ where R and R' are the same as defined previously and may be independently selected, R" is hydrogen or the same as R, and a is 0, 1 or 2; or R$_a$Si(NR'"COR')$_{4-a}$ where R and R' are the same as defined previously, R'" is a one to forty carbon atom monovalent hydrocarbon radical, R, R' and R'" may each be independently selected, and a is 0, 1 or 2. Preferably R, R' and R'" are selected from the group consisting of methyl, ethyl, n-propyl, i-propyl, trifluoropropyl, n-butyl, i-butyl, t-butyl, phenyl and tolyl.

Some non-limiting examples of these organosilicon compounds are: methyltrimethoxysilane, N-aminoethylaminopropyltrieehoxysilane, methyltris(N,N-diethylaminoxy) silane, methyltris(methylethylketoximo) silane, methyltris(dimethylketoximo)silane, vinyltris(methylethylketoximo)silane, vinyltris(dimethylketoximo) silane, methyltriacetoxysilane, ethyltriacetoxysilane, vinyltriacetoxysilane, methyltris(N-butylamino)silane, and methyltris(cydohexylamino)silane, methyltris(N-methylacetamido)silane.

The organosilicon compounds (B) are generally used in such an amount that at least one mole of the silicon compound exists per gram equivalent of the reactive end groups of the organopolysiloxane (A). More preferably, the organosilicon compound, (B), is generally used in an amount ranging from about 1 to about 15 parts by weight, most preferably (B) is used in amounts ranging from about 1 to about 10 parts by weight relative to component (A).

Component (C) comprises a non-ionic surfactant compound selected from the group of non-ionic surfactants consisting of polyethylene glycol, polypropylene glycol, ethoxylated castor oil, oleic acid ethoxylate, alkylphenol ethoxylates, copolymers of ethylene oxide (EO) and propylene oxide (PO) and copolymers of silicones and polyethers (silicone polyether copolymers) in an amount ranging from about 0.10 weight percent to about 4.00 weight percent based on the total amount of components (A) and (B), preferably an amount ranging from about 0.20 weight percent to about 3.00 weight percent based on the total amount of components (A) and (B), more preferably an amount ranging from about 0.70 weight percent to about 2.00 weight percent based on the total amount of components (A) and (B), and most preferably an amount ranging from about 0.80 weight percent to about 1.30 weight percent based on the total amount of components (A) and (B).

Component (D) may comprise a reinforcing filler or non-reinforcing filler or an appropriate mixture of both. Reinforcing fillers may be fumed silica, precipitated silica, hydrophobicized precipitated silica, hydrophobicized fumed silica, carbon black, titanium dioxide, ferric oxide, aluminum oxide, and other metal oxides. Non-reinforcing fillers may be calcium carbonate, diatomaceous earth, calcium silicate, zirconium silicate, talc, and bentonite. Fibrous materials such as asbestos, glass fibers, or organic fibers are also useful fillers. The amount of filler used in an RTV composition is selected as desired so as to not interfere with the purposes of the instant invention.

Component (E) comprises a condensation catalyst such as dialkyltincarboxylates, alkyl titanates, organosiloxy titanium compounds, and various other condensation catalysts known in the art.

Component (F) may comprise various additives such as pigments, dyes anti-oxidants, flame retardants, UV stabilizers, adhesion-enhancing agents, thermal stabilizing agents, mildewstats, fungicides, anti-microbials and the like in various combinations ranging from about 0.01% by weight of the sum of components (A) and (B) up to about 20% by weight.

In referring to an acetoxy, ketoximo, or alkoxy silicon sealant, applicants define such as a sealant having the general composition previously defined where the end groups of the organopolysiloxane component (A) are acetoxy, ketoximo, or alkoxy groups, respectively. By alkoxy groups applicants define alkoxy to include both alkyl-, aryl- and alkylaryl-substituted alkoxy groups.

Stringiness is measured by utilizing a test jig holding a caulking cartridge at a standard 45° angle to a movable surface, different angles of delivery may be employed without departing from the spirit of the instant process. The nozzle of the caulking cartridge is cut to a standardized 0.375" outside diameter, larger or smaller standardized nozzle diameters may be utilized without departing from the spirit of the instant process. A small amount of sealant is extruded onto the movable surface, which is protected by a layer of parafilm. The movable surface is engaged at speed of 300 inches per minute and begins moving. When the tail of the bead of sealant breaks from the caulking cartridge the test is complete. Stringiness is defined as the length traveled when the sealant bead breaks off from the caulking cartridge as measured from the base of the applied bead to the break. Shorter travel lengths of the sealant bead indicate reduced stringiness. As shown in the appended examples, an acceptable stringiness measurement is 3.5 inches or less.

The measurement of stringiness is easily accomplished by modifying a commercially available apparatus known as a Release and Adhesion Tester to accommodate a caulking gun wherein a tube containing RTV sealant, identical to those available at retail, may be inserted. The caulking gun is held at an angle of 45 degrees to the surface, close to the surface but not actually touching. The experiments reported had a separation of the tip of the caulking tube, the sealant delivery device, from the surface of 3 mm; other small distances could be used and might change the numbers obtained, but it is not anticipated that in a comparison of large numbers of sealant candidates that the general trend of the data obtained would be materially different. The surface upon which the sealant is being deposited is a movable surface, typically a movable sled which is moved at a standard speed away from the caulking tube after the initial bead of sealant has been deposited on the surface. The surface is usually protected by a non-adhesive, disposable covering such as a sheet of polyethylene, Parafilm, to minimize clean-up after the test is completed.

The apparatus used for the tests described in the experimental section was a model number 80-14-00 Release and Adhesion Tester available from Testing Machines, Inc. of Amityville, LI, N.Y. The modification was removal of the force gauge. Other machines having movable beds that should be adaptable to the purposes of the test are: model number SP-101B Slip/Peel Tester, model number SP-102B-3M90 Extended Capability Peel Tester, and model number ZPE-1000 High Rate Peel Tester available from IMASS, Inc. of Accord, Mass. All of these machines have a movable horizontal bed capable of moving at various speeds.

The essential features of the test are 1) application of the sealant to the surface at a constant angle, 2) moving the surface upon which the sealant has been applied away from the sealant source at a constant rate of speed, 3) stopping the motion of the movable surface when the sealant bead breaks off from the sealant source, and 4) measuring the length of any sealant string formed by the test process. It is reasonable to assume that there are several different mechanical configurations of commercially available laboratory equipment that will enable these process steps. Further, depending on the application rate of the uncured sealants being tested, i.e., higher or lower viscosity, the rate at which the movable surface is moved away from the sealant delivery device may be raised or lowered accordingly to provide meaningful data. The speed of the movable surface for purposes of this test ranges from about 0.2 inches per second to about 20 inches per second, preferably from about 0.5 inches per second to about 15 inches per second, more preferably from about 1 inch per second to about 10 inches per second, and most preferably from about 4 inches per second to about 6 inches per second when sealants of the compositions instantly disclosed are being evaluated. The utility of this process is that it provides a means of determining a minimum performance level for a particular sealant application, a means of reproducibly measuring such performance, calibrating such performance to a maximum string length, and comparing the string lengths among a series of sealant compositions to determine the most preferred composition for a given intended application. By application, Applicants mean sealing two similar or dissimilar materials. Thus, a sealant application to effect a seal between metal and glass will be different from a sealant application where it is desired to effect a seal between glass and wood. The preferred composition will vary depending on the materials between which it is desired to effect a seal and the preferred properties will thus also vary. The utility of this process is that it provides standard conditions to measure the stringiness of a particular sealant composition and compare the number thus obtained to the number obtained from measuring the stringiness of other sealant compositions, thereby affording a means of selecting a particular composition for a particular application. In this manner, desirable or undesirable features of various sealant compositions may be evaluated and the best composition selected for a particular application.

All U.S. patents referenced herein are herewith and hereby explicitly incorporated by reference. When the chemical term alkyl is used generically as in alkyl phenol the term is intended to mean monovalent hydrocarbon radicals containing from one to about forty carbon atoms which may be saturated or unsaturated and which may also contain substituent aromatic groups.

The following examples of the instant invention are illustrative only and are not to be construed as limitations upon the appended claims. The comparative examples are presented among other purposes for the purpose demonstrating the utility of the stringiness measurement for improving the properties of various sealant compositions.

EXPERIMENTAL

Example 1

This experiment demonstrates the effectiveness of the addition of 1.5 weight percent of a silicone polyether surfactant in an acetoxy sealant formulation for reducing stringiness. The two sealant formulations differed only in that 1.5 weight percent of a silicone polyether surfactant was added to the second formulation. The sealant composition was 72.74 weight percent dimethyl silicone oil, 6.00 weight percent dimethyl, 8.87 weight percent fumed or pyrogenic silica, 0.10 weight percent aluminum stearate and 4.00 weight percent of a catalyst solution. The catalyst solution consisted of the following components: 72.2664 weight percent methyltriacetoxysilane, 27.1371 weight percent of di-tertiary-butoxydiacetoxysilane and 0.5964 weight percent of dibutyl tin dilaurate. The sealants were tested for physical properties after curing for 7 days at 75° C. and 50 percent relative humidity. The processing and physical properties of the control and the control plus the non-ionic surfactant are set forth in Table 1.

TABLE 1

Reduced Stringiness with Incorporation of Silicone Polyether Surfactant

| Measurement | Control | Control plus 1.5 wt. % Surfactant |
|---|---|---|
| Application Rate, g/min. | 265 | 215 |
| Tack Free Time, min. | 13 | 11 |
| Boeing Flow, in. | 0.10 | 0.05 |
| Shore A Hardness | 20 | 21 |
| Tensile, psi | 230 | 455 |
| % Elongation | 470 | 670 |
| Modulus at 100%, psi | 60 | 75 |
| Stringiness, in. | >5 | 1.5 |
| Heat Aged Properties, 24 Hr. At 100° C. | | |
| Shore A Hardness | 19 | 22 |
| Tensile, psi | 260 | 300 |
| % Elongation | 490 | 495 |
| Modulus at 100%, psi | 60 | 70 |
| Peel Adhesion Properties C628 | | |
| Glass, lbs. Pull | 28 | 32 |
| % Cohesive Failure | 100 | 100 |
| Alclad Aluminum, lbs. Pull | 24 | 28 |
| % Cohesive Failure | 100 | 100 |
| Mill Finished Aluminum, lbs. Pull | 17 | 30 |
| % Cohesive Failure | 100 | 100 |
| Anodized Aluminum, lbs. Pull | 24 | 35 |
| % Cohesive Failure | 100 | 100 |

Example 2

This experiment demonstrates the effectiveness of the addition of 1.0 weight percent of a silicone polyether surfactant in an acetoxy sealant formulation for reducing stringiness. The two sealant formulations differed only in that 1.0 weight percent of a silicone polyether surfactant was added to the second formulation. The sealant composition was 72.74 weight percent dimethyl silicone oil, 6.00 weight percent dimethyl, 8.87 weight percent fumed or pyrogenic silica, 0.10 weight percent aluminum stearate and 4.00 weight percent of a catalyst solution. The catalyst solution consisted of the following components: 72.2664 weight percent methyltriacetoxysilane, 27.1371 weight percent of di-tertiary-butoxydiacetoxysilane and 0.596 weight percent of dibutyl tin dilaurate. The sealants were tested for physical properties after curing for 7 days at 75° C. and 50 percent relative humidity. The processing and physical properties of the control and the control plus the surfactant are set forth in Table 2.

TABLE 2

Reduced Stringiness with Incorporation of Silicone Polyether Surfactant

| Measurement | Control | Control plus 1.0 wt. % Surfactant |
|---|---|---|
| Application Rate, g/min. | 240 | 145 |
| Tack Free Time, min. | 18 | 18 |
| Boeing Flow, in. | 0.10 | 0.05 |
| Shore A Hardness | 17 | 16 |
| Tensile, psi | 250 | 200 |
| % Elongation | 515 | 460 |
| Modulus at 100%, psi | 60 | 55 |
| Stringiness, in. | >5 | 2.5 |
| Heat Aged Properties, 168 Hr. At 50° C. | | |
| Shore A Hardness | 14 | 14 |
| Tensile, psi | 215 | 215 |
| % Elongation | 550 | 545 |
| Modulus at 100%, psi | 50 | 50 |

Example 3:

This experiment demonstrates the effectiveness of the addition of 1.0 weight percent of polyethylene glycol surfactant in an acetoxy sealant formulation that also contains an organic plasticizer for reducing stringiness. The two sealant formulations differed only in that 1.0 weight percent of a polyethylene glycol surfactant was added to the second formulation. The sealant composition was 72.00 weight percent dimethyl silicone, 14.80 weight percent polybutene polymer, 8.90 weight percent fumed or pyrogenic silica, 0.10 weight percent aluminum stearate, 0.2 weight percent polypropylene glycol and 4.00 weight percent of a catalyst solution. The catalyst solution consisted of the following components: 72.2664 weight percent methyltriacetoxysilane, 27.1371 weight percent of di-tertiary-butoxydiacetoxysilane and 0.5964 weight percent of dibutyl tin dilaurate. The sealants were tested for physical properties after curing for 7 days at 75° C. and 50 percent relative humidity. The processing and physical properties of the control and the control plus the surfactant are set forth in Table 3.

TABLE 3

Reduced Stringiness with Incorporation of Polyethylene Glycol Surfactant

| Measurement | Control | Control plus 1.0 wt. % Surfactant |
|---|---|---|
| Application Rate, g/min. | 462 | 423 |
| Tack Free Time, min. | 16 | 17 |
| Boeing Flow, in. | 0.10 | 0.10 |
| Shore A Hardness | 23 | 22 |
| Tensile, psi | 160 | 205 |
| % Elongation | 285 | 345 |
| Modulus at 100%, psi | 70 | 70 |
| Stringiness, in. | 4.5 | 1.25 |
| Heat Aged Properties, 168 Hr. At 50° C. | | |
| Shore A Hardness | 18 | 12 |
| Tensile, psi | 185 | 185 |
| % Elongation | 370 | 450 |
| Modulus at 100%, psi | 60 | 45 |

Example 4

Using a 30 mm Werner-Pfleiderer (WP) twin screw extruder, a methoxy curing 1-part, surfactant free, RTV composition, referred to as "composition 1" was produced as follows:

RTV COMPOSITION 1

(1) 100 parts by weight of an alpha, omega-methyldimethoxy terminated PDMS polymer having a viscosity of 125,000 cps;

(2) 18.8 parts by weight of a D4 treated, reinforcing fumed silica filler;

(3) 20.6 parts by weight of an alpha, omega-trimethylsilyl terminated PDMS fluid having a viscosity of 100 cps;

(4) 10.2 parts by weight of a 50 centipoise "M,D,T" silanol fluid;

(5) 3.1 parts by weight of hexamethyldisilazane hydroxy/methanol scavenger;

(6) 0.8 parts by weight of methyltrimethoxysilane crosslinker;

(7) 1.6 parts by weight aminoethylaminopropyltrimethoxysilane adhesion promoter; and (8) 0.23 parts by weight of a 1:1 molar ratio of dibutyltin diacetate and dibutyltin dilaurate.

Sections 1-10 of the extruder were heated to 75° F. Extruder sections 11-14 were cooled with 0° F. glycol coolant. To WP barrel 1, there was continuously metered in alpha, omega-methyldimethoxy terminated PDMS polymer having a viscosity of 125,000 cps and D4 treated, reinforcing fumed silica filler. To WP barrel 6, there was continuously metered in alpha, omega-trimethylsilyl terminated PDMS fluid having a viscosity of 100 centipoise at 25° C., 50 centipoise "M,D,T" silanol fluid, hexamethyldisilazane hydroxy/methanol scavenger, methyltrimethoxysilane crosslinker, aminoethylaminopropyltrimethoxysilane adhesion promoter, and a solution of a 1:1 molar ratio of dibutyltin diacetate and dibutyltin dilaurate. A 6 mm Hg de-airing vacuum was applied at WP barrel 11. RTV sealant was produced at a rate of 40 lb./hr at a WP exit temperature of 25°–35° C.

Twenty-four hours after production, composition 1 was tested for degree of stringiness and application rate. Results are shown in table 4. Acceptable stringiness value is 3.5 inch maximum. Acceptable application rate value is 120 gm/min minimum.

Example 5

Non-ionic surfactant containing RTV compositions were prepared using the same base RTV formulation and continuous WP mixing procedure as described in example 1. Composition 1 type RTV sealants were prepared containing 1.0 parts by weight, per 100 parts by weight alpha, omega-methyldimethoxy terminated PDMS polymer described in example 4, of the of the following commercial non-ionic surfactants:

| RTV Composition No. | Non-ionic surfactant | Type | Source |
|---|---|---|---|
| 2 | SF 1023 | Silicone Polyether Copolymer (SPEC) | GE Silicones |
| 3 | SF 1550 | SPEC | GE Silicones |
| 4 | SF 1288 | SPEC | Ge Silicones |
| 5 | Pluriol E-200 | Polyethylene Glycol (PEG) | BASF |
| 6 | Pluriol E-300 | PEG | BASF |
| 7 | Pluriol E-400 | PEG | BASF |
| 8 | Pluriol E-600 | PEG | BASF |
| 9 | Pluriol P-600 | PEG | BASF |
| 10 | Pluriol P-900 | PEG | BASF |
| 11 | Pluriol P-2000 | PEG | BASF |
| 12 | Pluriol P-4000 | PEG | BASF |
| 13 | Pluronic 25R2 | Ethylene oxide propylene oxide block copolymer (EO-PO) | BASF |
| 14 | Pluronic 31R1 | EO-PO | BASF |
| 15 | Pluronic L44 | EO-PO | BASF |
| 16 | Pluronic L62 | EO-PO | BASF |
| 17 | Pluronic L64 | EO-PO | BASF |
| 18 | Pluronic L92 | EO-PO | BASF |
| 19 | Pluronic L101 | EO-PO | BASF |
| 20 | Pluracol P410 | Unknown Non-ionic (UNI) | BASF |
| 21 | Pluracol 628 | UNI | BASF |
| 22 | Pluracol 710 | UNI | BASF |
| 23 | Pluracol 735 | UNI | BASF |
| 24 | Pluracol 975 | UNI | BASF |
| 25 | Pluracol P1010 | UNI | BASF |
| 26 | Pluracol 1250D | UNI | BASF |
| 27 | Pluracol 4000D | UNI | BASF |
| 28 | Pluracol W5100N | Polyalkoxy polyether | BASF |
| 29 | Pluracol | PEG | BASF |
| 30 | Pluracol | PEG | BASF |
| 31 | Pluracol | PEG | BASF |
| 32 | Pluracol | PEG | BASF |
| 33 | Pluracol | PEG | BASF |
| 34 | Iconol TDA-9 | Tridecyl alcohol ethoxylate | BASF |
| 35 | Iconol OP-10 | Octylphenol ethoxylate | BASF |
| 36 | Tetronic 304 | ethylene propylene oxide ethylene diamine block copolymer | BASF |
| 37 | Polytergent SLF-18 | UNI | Olin |
| 38 | Polytergent SL-22 | UNI | Olin |
| 39 | Polytergent SL-62 | UNI | Olin |
| 40 | Polytergent P-17-A | UNI | Olin |
| 41 | Colorsperse 188A | Dioleate | Henkel |
| 42 | Emulan A | UNI | BASF |
| 43 | Emulan EL | UNI | BASF |
| 44 | Emulan OK5 | Ethoxylated fatty alcohol | BASF |
| 45 | Emulan ELP | Ethoxylated castor oil | BASF |
| 46 | Emulan PO | Alkylphenol ethoxylate | BASF |
| 47 | Liponic EG1 | Ethoxylated glycerin | LIPO |

-continued

| RTV Composition No. | Non-ionic surfactant | Type | Source |
|---|---|---|---|
| 48 | Liponic EG7 | Ethoxylated glycerin | LIPO |
| 49 | Liponate GC | Caprylic-capric triglyceride | LIPO |
| 50 | Liponate PC | Propylene glycol dicaprylate | LIPO |
| 51 | Lipocal L4 | Polyoxyethylene ether | LIPO |
| 52 | Ucon LB65 | Ethylene oxide propylene oxide polyglycol (EO-PO-PG) | Union Carbide |
| 53 | Ucon LB135 | EO-PO-PG | Union Carbide |
| 54 | Ucon LB285 | EO-PO-PG | Union Carbide |
| 55 | Triton X-100 | Ethylene oxide glycol | Union Carbide |

24 hours after production, composition 2–55 were tested for degree of stringiness (First Impression Quality Stringiness Test). Results are shown in Table 4.

Example 6

Example 4 was repeated with the addition of 0.80 parts by weight silicone polyether copolymer surfactant, per 100 parts by weight alpha, omega-methyldimethoxy terminated PDMS polymer described in example 4, (composition #56). Stringiness testing results are shown in table 1.

Example 7

Example 4 was repeated with the addition of 0.40 parts by weight silicone polyether copolymer surfactant, per 100 parts by weight alpha, omega-methyldimethoxy terminated PDMS polymer described in example 4, (composition #57). Stringiness testing results are shown in table 4.

Example 8

Example 4 was repeated with the addition of 1.7 parts by weight silicone polyether copolymer surfactant, per 100 parts by weight alpha, omega-methyldimethoxy terminated PDMS polymer described in example 4, (composition #58). Stringess testing results are shown in table 4.

Example 9

Example 4 was repeated with the addition of 0.40 parts by weight Pluriol E200 surfactant, per 100 parts by weight alpha, omega-methyldimethoxy terminated PDMS polymer described in example 4, (composition #59). Stringiness testing results are shown in table 4.

Example 10

Example 4 was repeated with the addition of 0.80 parts by weight Pluriol E200 surfactant, per 100 parts by weight alpha, omega-methyldimethoxy terminated PDMS polymer described in example4, (composition #60). Stringiness testing results are shown in table 4.

Example 11

Example 4 was repeated with the addition of 1.70 parts by weight Pluriol E200 surfactant, per 100 parts by weight alpha, omega-methyldimethoxy terminated PDMS polymer described in example 4, (composition #61). Stringiness testing results are shown in table 4.

TABLE 4

RTV SURFACTANT EVALUATION

| RTV Composition # | Stringiness, inch | Application Rate, gm/min |
|---|---|---|
| 1 | 8.5 | 294 |
| 2 | 4.5 | 265 |
| 3 | 3.5 | 219 |
| 4 | 2.0 | 145 |
| 5 | 1.0 | 138 |
| 6 | 2.0 | 162 |
| 7 | 4.0 | 198 |
| 8 | 5.0 | 215 |
| 9 | 4.5 | 207 |
| 10 | 4.0 | 219 |
| 11 | 4.0 | 223 |
| 12 | 4.5 | 201 |
| 13 | 4.5 | 233 |
| 14 | 4.5 | 217 |
| 15 | 4.0 | 228 |
| 16 | 1.5 | 204 |
| 17 | 3.0 | 235 |
| 18 | 3.0 | 191 |
| 19 | 2.5 | 168 |
| 20 | 5.5 | 241 |
| 21 | 2.5 | 198 |
| 22 | 4.5 | 249 |
| 23 | 0.0 | 84 |
| 24 | 4.5 | 202 |
| 25 | 3.5 | 183 |
| 26 | 2.5 | 168 |
| 27 | 4.0 | 219 |
| 28 | 4.0 | 229 |
| 29 | 1.5 | 138 |
| 30 | 1.5 | 144 |
| 31 | 2.0 | 156 |
| 32 | 2.5 | 156 |
| 33 | 3.5 | 185 |
| 34 | 3.5 | 162 |
| 35 | 4.0 | 172 |
| 36 | 1.5 | 138 |
| 37 | 4.5 | 209 |
| 38 | 4.5 | 211 |
| 39 | 4.5 | 235 |
| 40 | 4.5 | 213 |
| 41 | 4.5 | 239 |
| 42 | 4.5 | 220 |
| 43 | 5.0 | 241 |
| 44 | 6.0 | 229 |
| 45 | 3.0 | 171 |
| 46 | 3.5 | 182 |
| 47 | 2.0 | 162 |
| 48 | 1.0 | 114 |
| 49 | 2.0 | 174 |
| 50 | 5.5 | 214 |
| 51 | 4.0 | 199 |
| 52 | 4.5 | 189 |
| 53 | 5.5 | 238 |
| 54 | 3.5 | 169 |
| 55 | 4.5 | 197 |
| 56 | 2.5 | 162 |
| 57 | 4.5 | 246 |
| 58 | 1.5 | 126 |
| 59 | 3.5 | 188 |
| 60 | 2.5 | 144 |
| 61 | 2.5 | 126 |

The results shown in Table 4 demonstrate that a significant portion of the surfactants tested do not produce a stringiness measurement of 3.5 inches or less. Therefore not all non-ionic surfactants work to produce a reduction in stringiness of the room temperature vulcanizable sealants prepared and tested. Since only some of the non-ionic surfactants succeed in reducing stringiness, the reduction in stringiness by these surfactants is necessarily unexpected. Additional experiments demonstrated that cationic as well as anionic surfactants interfered with the cure mechanism and therefore these types of surfactants are unsuitable for reducing stringiness.

Having described the invention, that which is claimed is:

1. A process for measuring the stringiness of uncured room temperature vulcanizable sealant compositions comprising:
   (a) delivering said sealant onto a movable surface by means of a sealant delivery device whereby a bead of sealant is deposited onto said movable surface;
   (b) stopping the delivery of said sealant onto said movable surface;
   (c) moving said bead of sealant on said movable surface away from said sealant delivery device by moving said movable surface away from said sealant delivery device whereby a string of sealant is formed between said bead of sealant and said sealant delivery device until said string of sealant breaks off from said sealant delivery device;
   (d) stopping said movable surface; and
   (e) measuring the length of said string of sealant.

2. The process of claim 1 wherein said sealant delivery device is selected from the group consisting of a Release and Adhesion Tester, a Slip/Peel Tester, an Extended Capability Peel Tester, and a High Rate Peel Tester.

* * * * *